(12) United States Patent
Schweitzer et al.

(10) Patent No.: US 6,371,615 B1
(45) Date of Patent: Apr. 16, 2002

(54) METHOD AND APPARATUS FOR DETERMINING FLUOROPHORES ON OBJECTS, ESPECIALLY ON THE LIVING OCULAR FUNDUS

(75) Inventors: Dietrich Schweitzer, Neustadt/Oria; Achim Kolb, Kahla; Martin Hammer, Jena; Eike Thamm, Maua, all of (DE)

(73) Assignee: Friedrich-Schiller-Universität Jena Buero für Furschungstransfer-Sachgebiet Schutzrechte, Jena (DE)

( * ) Notice: Subject to any disclaimer, the term of this patent is extended or adjusted under 35 U.S.C. 154(b) by 0 days.

(21) Appl. No.: 09/561,903

(22) Filed: May 1, 2000

(30) Foreign Application Priority Data

Apr. 29, 1999 (DE) ........................................ 199 20 158

(51) Int. Cl.⁷ .............................................. A61B 3/10
(52) U.S. Cl. ...................................................... 351/221
(58) Field of Search ................................ 351/205, 206, 351/221; 600/476; 25/340, 458.1, 459.1, 461.2; 356/311, 318, 417

(56) References Cited

U.S. PATENT DOCUMENTS

| | | | |
|---|---|---|---|
| 4,213,678 A | 7/1980 | Pomerantzeff et al. | 351/7 |
| 4,569,345 A | 2/1986 | Manes | 128/303.14 |
| 4,632,550 A | 12/1986 | Hara et al. | 356/311 |
| 4,662,748 A | 5/1987 | Tanaka et al. | 356/317 |
| 4,786,170 A | * 11/1988 | Groebler | 356/318 |
| 5,148,031 A | * 9/1992 | Kamalov et al. | 250/458.1 |
| 6,055,451 A | * 4/2000 | Bambot et al. | 600/476 |

FOREIGN PATENT DOCUMENTS

| | | |
|---|---|---|
| DE | 36 14 359 | 2/1987 |
| DE | 44 10 690 | 6/1995 |
| DE | 44 29 383 | 2/1996 |
| DE | 44 40 968 | 5/1996 |
| DE | 197 18 016 | 11/1998 |
| DE | 197 22 790 | 12/1998 |
| GB | 2 231 958 | 11/1990 |

OTHER PUBLICATIONS

Ghiggino et al., "Time–resolved Fluorescence Spectroscopy Using Pulsed Lasers", J. Phys. E: Sci. Instr., vol. 13 (1980), pp. 446–450.

Rughooputh et al., An Inexpensive Microprocessor–Controlled Spectrophotometer for Time–Resolved Flourescence Spectroscopy, Meas. Sci. Tech. 5 (1994), 384–388.

Hungerford et al., "Single–Photon Timing Detectors for Fluorescence Lifetime Spectroscopy", Meas. Sci. Technol. 7 (1996), pp. 121–135.

* cited by examiner

Primary Examiner—George Manuel
(74) Attorney, Agent, or Firm—Crowell & Moring LLP

(57) ABSTRACT

A method and apparatus for determining fluorophores on objects, especially on the living ocular fundus, which makes it possible to reliably distinguish at least partially overlapping fluorophores of objects in excitation and/or fluorescence spectra even if fluorescence intensities are very low and to select them for analysis, and optionally create a two-dimensional representation. The object (4), e.g., the ocular fundus for ophthalmological examinations, is illuminated point to point with a pulsed laser (1) and excited to autofluorescence with two-dimensional extension. The transient fluorescence light created after excitation by each laser pulse is detected in time-correlated individual photon counting (11). From the time behavior of the fluorescence light determined by individual photon counting for each site of autofluorescence, the fluorescence decay time constants are calculated, and conclusions are drawn therefrom regarding the excited fluorophores in the object (4). The time regime for time-correlated individual photon counting (11) is controlled by the detected pulses of the fluorescence-exciting laser light (1) and by the fluorescence light created on the object (4). The spatial fluorescence allocation in multiple scanning excitation is carried out via a routing unit (13) synchronized with the scanning system.

21 Claims, 1 Drawing Sheet

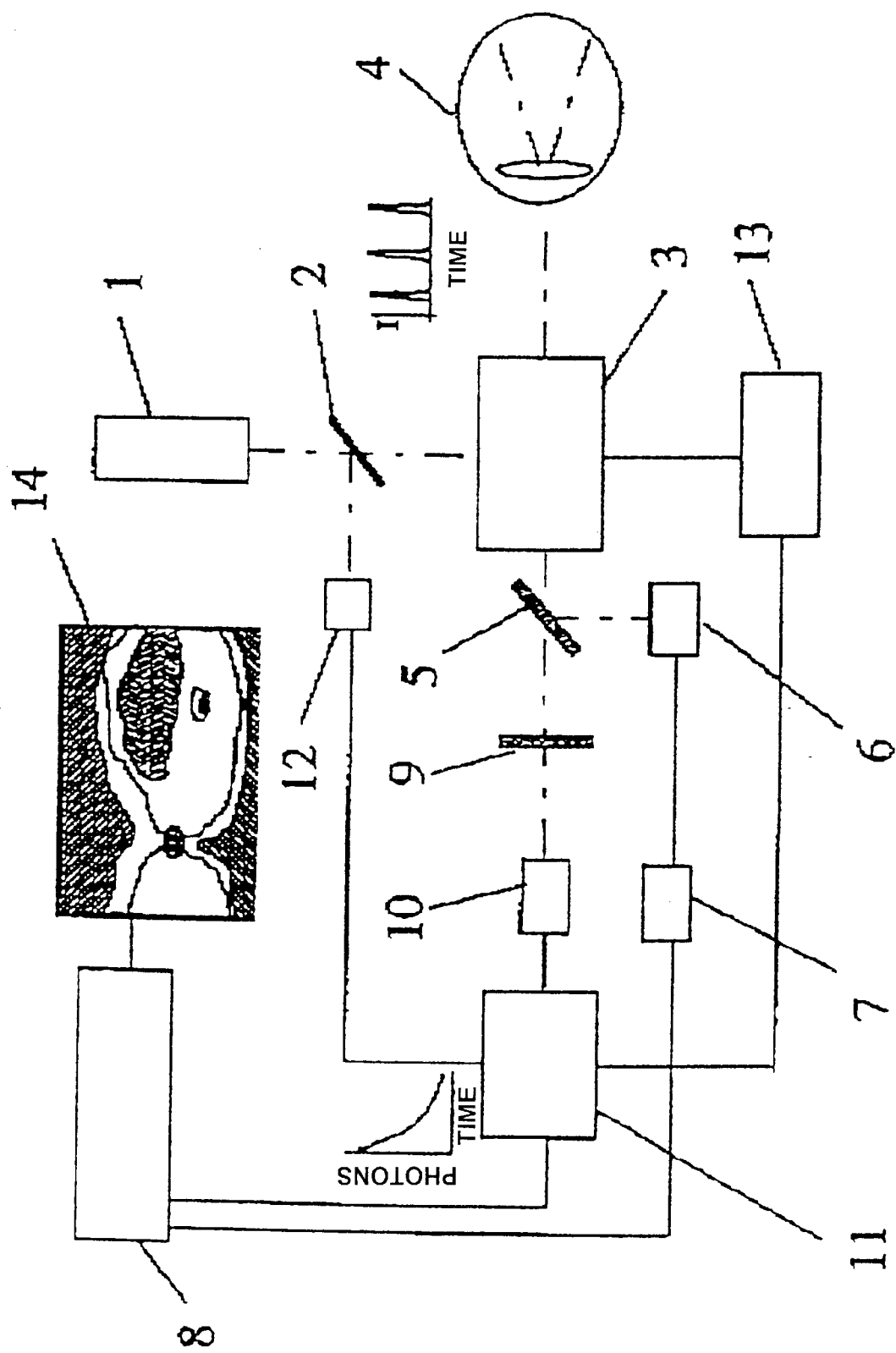

METHOD AND APPARATUS FOR DETERMINING FLUOROPHORES ON OBJECTS, ESPECIALLY ON THE LIVING OCULAR FUNDUS

BACKGROUND OF THE INVENTION

The invention relates to a method and an apparatus for determining fluorophores on objects, particularly on the living ocular fundus.

It is known in the art to use the natural fluorescence of objects to analyze these objects, for example to evaluate the metabolic state of living biological tissue, such as the ocular fundus in ophthalmological examinations. Exciting fluorescence in these objects thus makes it possible by optical evaluation of the autofluorescence in biological tissue to draw conclusions regarding the metabolic state of this tissue in a non-invasive manner. This requires an at least two-dimensional representation of the distribution of different fluorophores in the examined biological object. The examination of the vascular system of the ocular fundus in ophthalmological examinations by means of fluorescence markers, e.g., using intravenously injected sodium fluorescein (quantum efficiency approximately 1) or indocyanine green is state of the art in clinical routine. Autofluorescence on the ocular fundus can be measured only with very low quantum efficiency, with minor concentrations of fluorophores being present in addition. An added difficulty is that the limits for maximum permissible light exposure (American National Standard for Use of Lasers, ANSI 136.1—1993) must be complied with in the excitation of autofluorescence. U.S. Pat. No. 4,569,345 proposes to evaluate oxygenation of the retina by measuring autofluorescence at 520 nm and 540 nm, with excitation occurring at 450 nm. The disadvantage is that excitation at 450 nm results in absorption in the lens causing the lens to be excited to fluorescence. Based on the fluorescence measurements at 520 nm and 540 nm, it should be possible to compensate the influence of the ocular media, such as the lens, the aqueous humor, the cornea, and the vitreous body. Since the fluorescence of the lens is more intense than the fluorescence of the ocular fundus by approximately three orders of magnitude, it is almost impossible to obtain analyzable fluorescence signals from the ocular fundus in narrow wavelength ranges and to use these to compensate the influence of the ocular media. Radiation at 450 nm also excites lipid peroxidation products to fluorescence, which also show a measurable fluorescence at 540 nm. This means that the influences of lens fluorescence, of flavoproteins of the ocular fundus and of lipid peroxidation products on the ocular fundus cannot be determined separately by measuring the fluorescence at two wavelengths even if the fluorescence spectra of the individual fluorophores are known.

U.S. Pat. No. 4,213,678 discloses the principle of confocal scanning of the ocular fundus with a laser scanning ophthalmoscope. According to this principle, reflected images of the ocular fundus are obtained after a continuously radiant laser beam scanningly illuminates the ocular fundus and the reflected light is recorded by a detector. This technique, using fluorescent markers (sodium fluorescein, ICG), makes it possible to evaluate the retinal or choroidal vascular system. Furthermore, v. Rückmann et al. (*Br. J. Ophthalmol*, 1995; 79:407–412) have shown that particularly in age-related macular degeneration (AMD), autofluorescence can be detected if the ocular fundus is excited with 488 nm wavelength light and the total fluorescence light, globally above a 520 nm cut-off wavelength, is integrally recorded. Superimposing several autofluorescence images improves the signal-to-noise ratio.

Various procedures for characterizing primarily the pathological state by means of the autofluorescence spectra of specific fluorophores, e.g., in age-related macular degeneration (AMD), have been published. By exciting a relatively large area on the ocular fundus and measuring the autofluorescence spectrum, Delori et al. (*Invest Ophthalmol Vis Sci.*, 1995; 36:718–729) were able to show that the degradation product of lipid peroxidation, lipofuscin, largely determines the autofluorescence in AMD.

Using imaging spectrometry in which the autofluorescence spectra of all excited sites of the ocular fundus are measured simultaneously along a line after excitation to autofluorescence, Schweitzer et al. (*Invest. Ophthalmol Vis Sci.*, 1998; 38:387) showed that after excitation in various wavelength ranges autofluorescence can be excited for at least two fluorophores on the ocular fundus. While shorter wave autofluorescence is more pronounced in healthy eyes, a more pronounced long wave fluorescence spectrum is evident in AMD. Biological tissue, particularly that of the ocular fundus, has the characteristic that any possible radiation within the visible spectral region excites several fluorophores, the fluorescence spectra of which overlap. The quantum efficiency of the natural fluorophores is thereby very low. Since the ocular fundus contains the light-sensitive receptors of the eye, the excitation intensity must be small enough so as to exclude any damage. A clinical application of autofluorescence to characterize the metabolic state or its change at a given instant before morphological changes are detected furthermore requires a two-dimensional autofluorescence measurement with the highest possible spatial resolution, which also causes a reduction in the fluorescence light that can be detected from each site. The finer the spatial resolution per measuring point, the lower the measurable fluorescence intensity will be. An added problem particularly for measuring autofluorescence on the ocular fundus is the fact that the eye is a movable object that is able to focus on an object for only a limited time. The consequence of these particular examination conditions is that it is currently practically impossible to separate the fluorophores active on the ocular fundus by the different fluorescence spectra due to the overlapping fluorescence spectra and the poor signal-to-noise ratio with which autofluorescence on the ocular fundus can be measured.

There is considerable interest among persons skilled in the art, however, in the two-dimensional measurement of the autofluorescence of different fluorophores, especially on the ocular fundus, to identify the metabolic state, which is effectively impossible with the known methods and under the aforementioned special ophthalmological conditions.

SUMMARY OF THE INVENTION

It is therefore the aim of the invention to distinguish reliably at least partially overlapping fluorophores of objects in excitation and/or fluorescence spectra, even if fluorescence intensities are very low and to select them for analysis with the possibility of a two-dimensional representation.

In accordance with the invention, a method and an apparatus are proposed, with which the object, for example, the ocular fundus for ophthalmological examinations, is subjected to point-to-point illumination by pulsed laser light and excited to autofluorescence with two-dimensional extension. The transient fluorescence light created after excitation by each laser pulse is detected in time-correlated single photon counting. Based on the time fluorescence behavior for each site determined by time-correlated single photon counting, the fluorescence time constants are calculated. Since the fluorescence time constant is a characteristic feature for each fluorophore, the fluorescence time constants are used to draw conclusions regarding the fluorophores excited in the object. While it is not possible based on prior art to distinguish different fluorophores, particularly of the ocular fundus, in a space-resolved two-dimensional representation due to the overlapping fluorescence spectra and the extremely low fluorescence intensity as a consequence of the limited radiant excitation power specified by safety regulations, the fluorophores can be distinguished according to their different fluorescence decay time. Surprisingly it was found that the extremely weak fluorescence intensities measurable from the ocular fundus represent very good conditions for time-correlated individual photon counting. The technique of time-correlated individual photon counting requires that by means of a laser excitation pulse, a fluorescence photon will be registered only with a probability of 0.1. The excitation pulse rate must be high so that an analyzable decay behavior can be registered within a correspondingly short time. The time regime for the time-correlated individual photon counting is controlled by the detected pulses of the fluorescence-exciting laser light and the fluorescence light created on the object. From the register contents of counters into which the detected fluorescence photon is read after each excitation pulse corresponding to the delay time between the excitation pulse and the detected fluorescence photon, the decay times of the transient autofluorescence caused by pulse excitation are determined for each site of the object, based on which the fluorophores are distinguished.

Further advantageous preferred embodiments are described in more detail hereinafter.

BRIEF DESCRIPTION OF THE DRAWINGS

The invention will be described in greater detail with reference to an illustrative preferred embodiment shown in the accompanying drawing FIGURE, which is a schematic representation of an arrangement according to the invention for analyzing fluorophores on an ocular fundus.

DESCRIPTION OF PREFERRED EMBODIMENTS

The radiation of a pulsed laser 1 with a pulse length of less than 0.5 ns and a repetition rate of approximately 80 MHz is coupled into a laser scanning ophthalmoscope 3 via a partially transparent mirror 2 and illuminates the fundus of a patient's eye 4 to be examined point-to-point by deflecting the laser beam pulse in horizontal and vertical direction. To discriminate reflected light from the anterior eye media and to suppress fluorescence light excited in the anterior eye media, particularly the lens, the illumination beam path and the detection beam path are geometrically separated by an aperture diaphragm division in the plane of the aperture diaphragm of the patient's eye 4 (not shown in the drawing for reasons of clarity). The light reflected from the fundus of the patient's eye 4 undergoes descanning during the renewed pass through the laser scanning ophthalmoscope 3 and after deflection by a dichroic mirror 5 is recorded in known manner by a detector 6 on which the illuminated site of the ocular fundus was confocally represented. Via a frame grabber 7 synchronized with the scanner ophthalmoscope 3, the reflected images of the ocular fundus are read into a computer 8.

The radiation of pulsed laser 1 has a selectable wavelength, which in the present example is selected relatively short at 520 nm. This radiation excites fluorophores of the ocular fundus to transient fluorescence. The fluorescence light also undergoes descanning by the laser scanning ophthalmoscope 3 and strikes the dichroic mirror 5 whose properties are selected such that light in a wavelength range greater than 520 nm is transmitted through mirror 5 while the shorter wave fluorescence excitation light is reflected on mirror 5. The separation of fluorescence light and reflected light on the dichroic mirror 5 can also be selected such that the fluorescence light is reflected on the mirror while the light reflected from the patient's eye 4 is transmitted through the mirror. The fluorescence light subsequently passes through a rejection filter 9, which completely blocks any excitation light that may not have been sufficiently blocked by the dichroic mirror 5 as well as any intra-apparatus scattered light. The fluorescence light is registered by a highly sensitive fluorescence detector 10 connected to a unit 11 for time-correlated single photon counting.

In time-correlated single photon counting, in normal mode, a time process is started by each excitation pulse, which is stopped by the recorded individual fluorescence photons. The entire time process is divided into segments to which individual registers are assigned corresponding to the measured delay time between excitation pulse and fluorescence photons, which are sequentially counted up by one for each recorded fluorescence photon. After a sequence of excitation pulses have struck the ocular fundus, the contents of the individual counters of unit 11 represent the time decay behavior of the fluorescence light excited by the pulses at a site. From the time decay behavior of the fluorescence, the time constants (decay time) of the time fluorescence behavior is determined in computer 8. These fluorescence time constants are used to distinguish fluorophores and their concentration. A particular advantage of fluorophore distinction according to the invention by the decay behavior of the fluorescence light is that the analysis can be used independently of the fluorescence intensity and thus also for very low fluorescence intensities as they occur, for example, in ophthalmology. The fluorophores thus distinguishable in the fluorescence image of the fundus of the patient's eye 4 are determined in computer 8 based on the known allocations between decay time constant and fluorophore at a known excitation wavelength.

To be able to detect the fluorescence registered from the ocular fundus by time-correlated individual photon counting, time synchronization is effected between pulsed laser 1 and unit 11 for time-correlated individual photon counting. For this purpose, a portion of the laser excitation pulse is separated by the partially transparent mirror 2 and registered by a fast detector 12 (excitation detector). The output signal of this detector starts the time process of unit 11 for time-correlated individual photon counting. While taking into account the maximum permissible exposure, the transmission of the optical arrangement, and the quantum efficiency for the excitation of fluorescence light on the ocular fundus and the detector quantum efficiency, the output signal of fluorescence detector 10 created with a probability of approximately 0.1 stops the time process of unit 11 for time-correlated individual photon counting. The functional action of excitation pulse and detected fluorescence photon to generate the start and stop signal in the time process can in principle also be reversed (reversed mode) so that the fluorescence photon starts the time process and the next laser pulse for fluorescence excitation of the ocular fundus stops the time process.

Fluorescence in the patient's eye 4 is simultaneously excited with continuous scanning of the ocular fundus at a high laser pulse rate (in the present example a pulse rate of 80 MHz). Since the autofluorescent signal is very weak, integration must be effected over a certain time period, which due to the scanning motion of the excitation beam has the result that a certain area on the ocular fundus is scanned to obtain time-resolved fluorescence. Consequently, the spatial resolution for the two-dimensional representation of the time-resolved fluorescence is somewhat lower with approximately 50 µm than in the reflected image registered in parallel. To ensure allocation of the measured fluorescence decay curves to the corresponding site of the two-dimensional scanning, the scanning and descanning process, respectively, is synchronized in the laser scanning ophthalmoscope 3 with unit 11 for time-correlated individual photon counting via a router 13. Router 13 via the size of a time slot determines the spatial resolution with which the measured fluorescence photons are allocated to the fluorescence decay curve of a point during continuous scanning of the ocular fundus with the excitation laser beam.

In unit 11 for time-correlated individual photon counting, the decay curve of the autofluorescence is stored as the register content for each scanned picture element of the ocular fundus and is thus available for determining the fluorescence decay time for each picture element, which is executed in computer 8. In a two-dimensional representation on a monitor 14 connected to computer 8, the image of the calculated decay times encoded by gray-scale values or false colors in which areas of identical decay time can advantageously be color-marked is superimposed on the reflected image for better clinical interpretation. As the fluorescence time characteristics are separated, both the decay time constants corresponding to the type of the fluorophores and the prefactors representing the concentrations of the fluorophores are determined. The information on the type and the concentration of the fluorophores can be displayed in separate images or compressed into a single image. For example, the different fluorophores in their associated areas can be characterized by colors the intensity of which corresponds to the concentration. From the additive mixture of the colors, each of which corresponds to a certain concentration of fluorescent components present, a mixed color can be calculated corresponding to the concentration ratio of the fluorophores. The two-dimensional distribution of the fluorophores can also be output on a printer instead of, or in addition to, on the monitor 14. To effectively calculate and evaluate the two-dimensional images based on fluorescence decay time, the fluorescence drop over time, even in the case of several fluorescing components, is furthermore approximated by a monoexponential drop and the calculated effective decay time is used in the analysis.

Adjustable field apertures (not shown in the drawing) can be advantageously disposed both in front of detector 6 for the reflected light and in front of the fluorescence detector 10, to facilitate confocal registration of the excitation beam in various depths of the ocular fundus for the reflected light or for the fluorescence light.

Adding the contents of all registers of unit 11 for time-correlated individual photon counting for the time-dependent fluorescence behavior of each scanned point on the ocular fundus makes it possible to represent an image of the integral fluorescence intensity.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method for determining fluorophores on an object, said method comprising the steps of:
    illuminating the object point-to-point by pulsed laser light and exciting the object to fluorescence to produce resulting fluorescence light;
    scanning the object and detecting the resulting fluorescence light by time-correlated individual photon counting to obtain a representation of time/fluorescence behavior of the illuminated object for analysis;
    determining fluorescence decay times from the time/fluorescence behavior represented by the time-related individual photon count, and
    determining from the fluorescence decay times the properties of fluorophores excited to fluorescence in the object.

2. A method according to claim 1, wherein the object is a living ocular fundus.

3. A method according to claim 1, wherein the object is illuminated and excited to fluorescence by laser pulses with a pulse duration shorter than 0.5 ns, a repetition rate of approximately 80 MHz, and a wavelength of less than 520 nm.

4. A method according to claim 1, wherein the distribution of the fluorescence decay times is represented two-dimensionally in a fluorescence image of the object.

5. A method according to claim 4, wherein in addition to detection by time-correlated individual photon counting of the fluorescence light of the object produced by pulsed excitation, the reflected light of the object is simultaneously analyzed, and a reflected image is determined therefrom, which is superimposed on or compared with the fluorescence image of the object obtained by time-correlated individual photon counting.

6. A method according to claim 5, wherein light from the object is separated into fluorescent and reflected light components for independent detection, and wherein the fluorescence light is blocked for the spectral region of the reflected light and of any scattered light.

7. A method according to claim 1, wherein the distribution of the fluorophores determined from their fluorescence decay times is represented two-dimensionally in a fluorescence image of the object.

8. A method according to claim 7, wherein in the fluorescence image of the object, areas associated with different fluorophores are represented in different colors.

9. A method according to claim 1, wherein the time-correlated individual photon counting is started by detection of a pulse of laser light and stopped by detection of a pulse of fluorescence light.

10. A method according to claim 1, wherein the time-correlated individual photon counting is started by detection of a pulse of fluorescence light and stopped by detection of a pulse of laser light.

11. A method according to claim 1, wherein the time-correlated individual photon counting is spatially allocated in synchronization with the two-dimensional fluorescence excitation of the object.

12. An apparatus for determining fluorophores on an object comprising a laser and a laser scanning system for point-to-point illumination and two-dimensional fluorescence excitation of the object and for descanning of fluorescence light created by the fluorescence excitation on the object, wherein said laser for illumination and fluorescence excitation of the object is a pulsed laser; wherein the output of the laser scanning system at which the fluorescence light produced by pulsed excitation of the object and determined by space-resolved measurement exits is connected via a fluorescence detector with a time-correlated individual photon counter, and wherein the output of the time-correlated individual photon counter is connected to a computer for calculating and outputting corresponding fluorescence decay times of the fluorescence light produced by pulsed excitation.

13. An apparatus according to claim 12, wherein the pulsed laser is connected via beam guidance means and a detector with a time controller for the time-correlated individual photon counter.

14. An apparatus according to claim 12, wherein the output of the laser scanning system at which the fluorescence light produced by pulsed excitation of the object and determined by space-resolved measurement exits is connected with the fluorescence detector via a dichroic mirror.

15. An apparatus according to claim 14, wherein a rejection filter for blocking the spectral region of the reflected light from object and any scattered light is disposed before the fluorescence detector.

16. An apparatus according to claim 14, wherein a reflected light detector is arranged in a beam path of reflected light from the object diverted by the dichroic mirror, and said detector is connected with the computer via a frame grabber to detect a reflected image of the object.

17. An apparatus according to claim 12, wherein in order to synchronize the time-dependent counting process of the fluorescence photons with the spatial two-dimensional fluorescence excitation of the object, the laser scanning system is coupled via a router with a controller for the time-correlated individual photon counter.

18. An apparatus according to claim 12, further comprising an output device for displaying or storing measured fluorescence and reflected images.

19. An apparatus according to claim 18, wherein said output device is a display monitor.

20. An apparatus according to claim 12, further comprising an adjustable field aperture disposed before the fluorescence detector for detecting the fluorescence from different planes of the object.

21. An apparatus according to claim 12, further comprising an adjustable field aperture disposed before the reflected light detector for detecting the reflected light from different planes of the object.

* * * * *